United States Patent [19]

Becht et al.

[11] 4,179,057
[45] Dec. 18, 1979

[54] DISPOSABLE SURGICAL STAPLING INSTRUMENT

[75] Inventors: Carl T. Becht, Cincinnati; J. Charles Hueil, Loveland, both of Ohio

[73] Assignee: Senco Products, Inc., Cincinnati, Ohio

[21] Appl. No.: 961,740

[22] Filed: Nov. 17, 1978

[51] Int. Cl.² .................. A61B 17/04; B25C 5/02
[52] U.S. Cl. .............................. 227/19; 227/120; 227/127; 227/129
[58] Field of Search .............. 227/19, 120, 127, 129, 227/134

[56] References Cited
U.S. PATENT DOCUMENTS

| | | | |
|---|---|---|---|
| 2,874,384 | 2/1959 | Krone | 227/19 |
| 3,873,016 | 3/1975 | Fishbein | 227/19 |
| 4,109,844 | 8/1978 | Becht | 227/19 |

Primary Examiner—John McQuade
Attorney, Agent, or Firm—Frost & Jacobs

[57] ABSTRACT

A disposable surgical stapling instrument for forming and implanting surgical staples in the skin or fascia of a patient to close a wound or incision. The instrument comprises an elongated body having a forward portion and a rearward portion serving as a handle portion. The forward portion of instrument body houses a staple driver attached to a staple driver actuator and a return spring for the staple driver actuator. A surgical staple magazine assembly is affixed to the lower edges of the instrument body forward portion. An anvil plate, supporting a tow of surgical staples, is located within the magazine assembly. The anvil plate terminates at its forward end in a coextensive anvil surface. The magazine assembly contains a feeder assembly to constantly urge the row of staples toward the anvil surface to locate the forwardmost staple of the row thereon to be implanted and formed thereabout by the driver and to disengage a formed staple therefrom. The magazine assembly also provides a channel for the lower end of the staple driver and a staple retaining surface to minimize bending of the staple crown during the staple forming operation. The staple driver is shiftable between a retracted position and a staple forming position by means of a trigger pivotally mounted to the instrument body forward portion and operatively connected to the staple driver actuator.

16 Claims, 22 Drawing Figures

DISPOSABLE SURGICAL STAPLING INSTRUMENT

CROSS REFERENCE TO RELATED APPLICATION

The surgical stapling instrument of the present invention constitutes an improvement of that surgical stapling instrument taught in U.S. Pat. No. 4,109,844, issued Aug. 24, 1978 in the name of Carl T. Becht and entitled SURGICAL STAPLING INSTRUMENT.

BACKGROUND OF THE INVENTION

1. Field of the Invention

The invention relates to a surgical stapling instrument, and more particularly to such an instrument which may be of a single-use, disposable nature.

2. Description of the Prior Art

While the stapling instrument of the present invention may have many applications, it is particularly adapted for use as a surgical stapling instrument and will, for purposes of an exemplary showing, be so described. The surgical stapling instrument of the present invention could be so constructed as to be reusable, as will be briefly discussed hereinafter. Nevertheless, it is particularly well adapted to be inexpensively produced as a single-use, disposable instrument, and for that reason will be so described herein for purposes of an exemplary showing.

Recently surgeons have come more and more to the use of surgical staples (sometimes referred to as staple sutures), rather than conventional thread sutures, for the closing of wounds or incisions in the skin or fascia of a patient. This is true in part because the use of surgical staples is a far easier procedure. Of even greater importance, however, is the fact that the use of surgical staples is very much faster. Thus, the time required for suturing can be substantially reduced, thereby reducing the length of time the patient must be maintained under anesthesia.

Prior art workers have developed various types of surgical stapling instruments, examples of which are taught in U.S. Pat. Nos. 3,618,842; 3,643,851; 3,717,294; 3,837,555 and 3,873,016. In general, the prior art surgical stapling instruments are complex in construction and expensive to manufacture. These instruments do not lend themselves well to be so constructed as to be disposable. Prior art surgical staplers generally require a replaceable cartridge for the staples and a portion of the force required to actuate these instruments is expended in shifting a staple from a row thereof within the cartridge to an anvil means prior to formation of the staple about the anvil means. As a result, some prior art surgical stapling instruments require upwards of 20 pounds force to form and implant a surgical staple.

In the above mentioned U.S. Pat. No. 4,109,844, a disposable surgical stapler is taught. This surgical stapler is provided with an anvil plate terminating at its forward end in a coextensive anvil surface and slidably mounting a row of staples. Means are also provided to constantly urge and advance the row of staples along the anvil plate to place a forwardmost staple of the row on the anvil surface to be formed by a staple driver. The staple driver is shiftable between a normal upper position above and closely adjacent the forwardmost staple on the anvil surface and a lower position wherein it implants and forms the forwardmost staple.

The present invention provides a disposable surgical stapling instrument which represents an improvement over that of the above mentioned U.S. Pat. No. 4,109,844. The surgical stapling instrument of the present invention contains substantially all of the advantages of the surgical stapler taught in the above mentioned U.S. Pat. No. 4,109,844, including being disposable, light weight, inexpensive to manufacture and requiring very little force to operate it. In addition, the surgical stapling instrument of the present invention is characterized by a unique surgical staple magazine assembly and a unique driver-driver actuator-trigger assembly.

SUMMARY OF THE INVENTION

The disposable surgical stapling instrument of the present invention comprises an elongated hollow body having a forward portion and a rearward portion serving as a handle portion. The forward portion of the instrument body houses a staple driver attached to a staple driver actuator. The forwardmost inside surface of the forward body portion is provided with guide means for the staple driver-staple driver actuator assembly. The staple driver actuator has a pair of lugs extending laterally to either side thereof and through slots in the forward portion of the instrument body.

To the lower edges of the instrument body forward portion there is affixed a surgical staple magazine. The magazine is made up of upper and lower members. The lower member is adapted to receive an anvil plate which extends substantially the length thereof. At its forward end the anvil plate terminates in a coextensive anvil surface. The forwardmost end of the lower magazine member is provided with a notch so sized as to retain an unformed surgical staple, but to permit the passage therethrough of a formed surgical staple. The anvil plate is configured to mount a row of staples and a feeder shoe therefor. The upper member of the surgical staple magazine is adapted to be received in the lower member and to overlie the anvil plate, the row of staples and the feeder shoe. The upper magazine member mounts a double-coil spring which constantly urges the feeder shoe and thus the row of staples toward the anvil surface of the anvil plate. This results in the location of the forwardmost staple of the row on the anvil surface and the disengagement from the anvil surface of a formed staple, as will be described hereinafter. At the forward end of the surgical staple magazine, the upper and lower magazine members form a channel for the lower end of the staple driver. The upper magazine member also provides a staple retaining surface spaced above the anvil surface to minimize bending of the crown of a surgical staple during the staple forming operation.

The staple driver is shiftable (in the channel formed therefor in the surgical staple magazine) between a retracted position and a staple forming position in which it implants the forwardmost surgical staple of the row into the skin or fascia of the patient and forms the staple about the anvil surface of the anvil plate. Shifting of the staple driver is accomplished by means of a trigger pivotally mounted on the forward portion of the instrument body. The forwardmost end of the trigger engages the transverse lugs of the staple driver actuator. The trigger is pivotable between a normal position wherein the staple driver is in its retracted position and an actuated position wherein the staple driver is in its staple forming position.

The forward portion of the instrument body also houses a return spring. The return spring is in the form of a coiled compression spring, one end of which is mounted on a seat supported by the surgical staple magazine and the other end of which engages the staple driver actuator. The return spring biases the staple driver to its retracted position and at the same time biases the trigger to its normal position.

BRIEF DESCRIPTION OF THE DRAWINGS

FIG. 13 is a rear elevational view of the assembled magazine.

DESCRIPTION OF THE PREFERRED EMBODIMENTS

Figures 1, 1A:
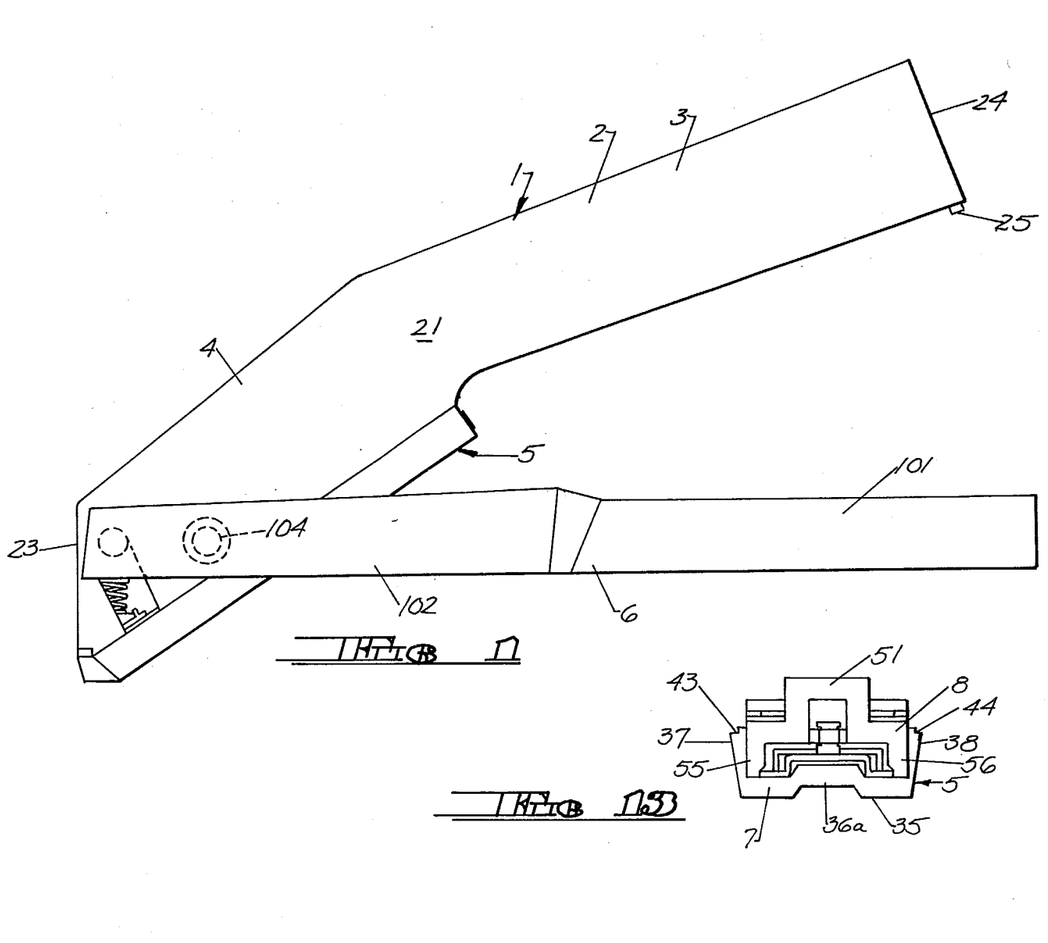
FIG. 1 is a side elevational view of the surgical stapling instrument of the present invention.
Figure 2:
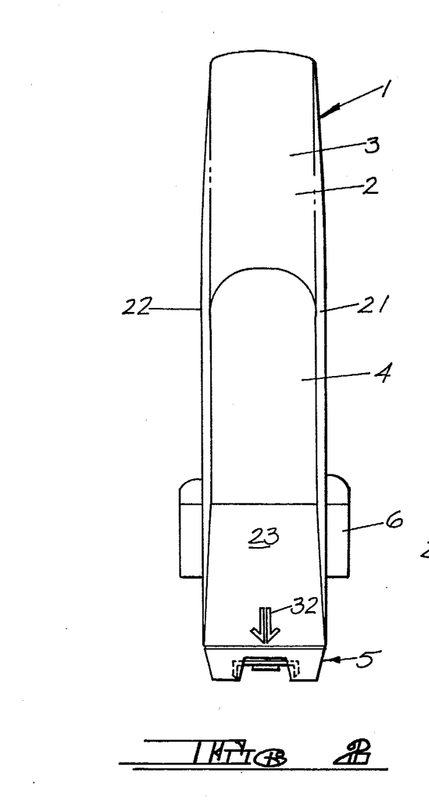
FIG. 2 is a front elevational view of the surgical stapling instrument of FIG. 1.
Figures 3, 4:
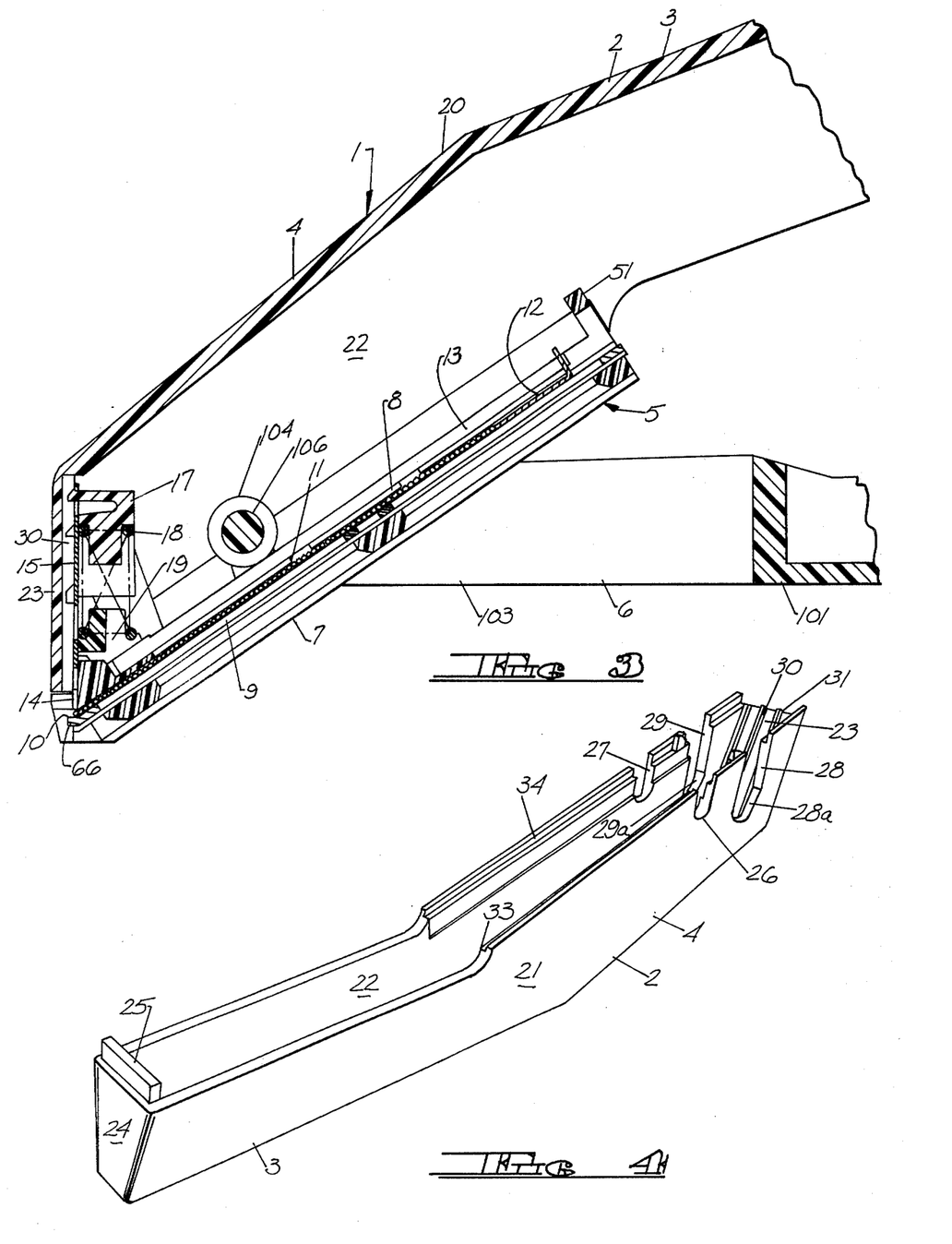
FIG. 3 is a fragmentary cross sectional view of the surgical stapling instrument of the present invention.
FIG. 4 is a perspective view of the surgical stapling instrument body.

In all of the Figures, like parts have been given like index numerals. Reference is first made to FIGS. 1 through 3 wherein the surgical stapling instrument is generally indicated at 1. The instrument comprises a body 2 having a rearward portion 3 which serves as a handle and a forward portion 4. It will be noted that the rearward portion 3 is angularly related to the forward portion 4 so that the instrument can more easily be held in its normal position of use, as illustrated in FIGS. 1 and 2. It will be understood by one skilled in the art that the position in which the instrument is held while being used is not limited to that shown in FIGS. 1 and 2 and depends primarily on the patient position and the area of the patient being sutured.

The forward portion 4 of the instrument body 2 includes a surgical staple magazine, generally indicated at 5. The surgical stapling instrument is actuated by a trigger 6.

Turning to FIG. 3, the primary components of the surgical stapling instrument are therein shown. Each of these components will be taken up in turn and described in detail. However, for a better understanding of the detailed descriptions to follow, the primary components will be called out with respect to FIG. 3. It will be noted that the magazine 5 is affixed to the lower edges of the forward portion 4 of body 2. The magazine 5 comprises a lower member 7, an upper member 8 and an anvil plate 9 located therebetween. The anvil plate 9 terminates at its forward end in a coextensive anvil surface 10. Slidably mounted on anvil plate 9 is a row of staples 11. Also slidably mounted on anvil plate 9 there is a feeder shoe 12 which is constantly urged toward anvil surface 10 by a double-coil spring 13. The forward end of magazine 5 provides a channel 14 for a staple driver 15 mounted within the forward portion 4 of instrument body 2. Staple driver 15 is affixed to a staple driver actuator 17. The trigger 6 is operatively connected to staple driver 17 to shift it and the staple driver 15, as will be described hereinafter. Finally, a return spring 18 is located within the forward portion 4 of the instrument body 2. The upper end of return spring 18 is in contact with staple driver actuator 17, and the lower end of the return spring is mounted on a return spring seat 19. The return spring 18 is intended to bias the staple driver 15 to its retracted position and at the same time to bias the trigger 6 to its normal position, all as will be described.

Reference is now made to FIG. 4. FIG. 4 is a perspective view of the body 2 of instrument 1. So that its interior may be shown, the body 2 is illustrated in inverted condition. The rearward or handle portion of the body is again shown at 3 and the forward portion is shown at 4. The angular relationship between these two portions of body 2 can again be seen. The body 2 is hollow having a top 20 (see FIG. 3) side walls 21 and 22, a front wall 23 and a rear wall 24. A lug 25 extends along and depends downwardly from rear wall 24. Lug 25 acts as a stop for the rearward end of trigger 6, when the trigger 6 is in its actuated position.

Side walls 21 and 22 have first notches 26 and 27 formed therein. The upper ends of notches 26 and 27 serve as bearings for pivoted trigger 6, as will be described hereinafter. Side walls 21 and 22 have second notches 28 and 29 formed therein. These notches are intended to accommodate the staple driver actuator 17, as will be shown.

The front wall 23 of body 2 has a pair of integral guide rails 30 and 31 on its inside surface. These guide rails are intended to cooperate with the staple driver 15 and staple driver actuator 17, as will be described and as is shown in FIG. 3. The exterior surface of front wall 23 may be provided with an indicia arrow 32 or the like (see FIG. 2) to assist the surgeon in properly aligning the instrument with respect to the wound or incision to be sutured. The body 2 of instrument 1 lends itself well to be molded of a plastic materials appropriate for use in a surgical environment.

The surgical staple magazine 5 is, as shown in FIGS. 1 through 3, affixed to the lowermost edges of side walls 21 and 22 and front wall 23 at the forward portion 4 of body 2. To this end, at the forward portion 4 of body 2, side wall 21 has a longitudinally extending interior notch 33 adjacent its bottom edge and interrupted by slots 26 and 28. Similarly, side wall 22, at the forward portion 4 of the body 2, has a substantially identical longitudinal notch 34, interrupted by slots 27 and 29. Portions of the lower member 7 of magazine 5 are received within the notches 33 and 34 and abut the lowermost edge of front wall 23. The magazine may be permanently affixed to the body 2 in any appropriate manner. Since the lower member 7 of magazine 5 may also be molded of an appropriate plastic material, this joinder may be accomplished by adhesive means, welding or the like, all as is well known in the art.

Figure 5:
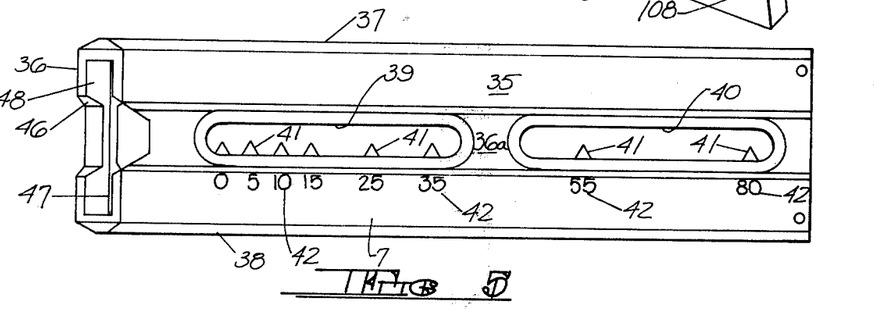
FIG. 5 is a bottom view of the lower member of the surgical staple magazine.
Figure 6:
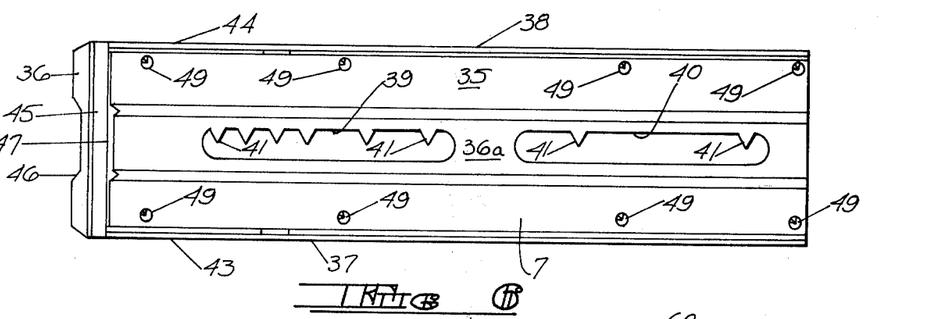
FIG. 6 is a top plan view of the lower member of the magazine.

In order to describe the surgical staple magazine 5, reference is first made to FIGS. 5 and 6 wherein its lower member 7 is illustrated from below and above, respectively. The lower member 7 has a bottom 35, a front wall 36 and side walls 37 and 38. The bottom 35 has a central and longitudinally extending raised portion 36a (see also FIG. 13). A pair of openings 39 and 40 may be provided in the raised portion 36a so that the surgeon may view therethrough the row 11 of staples. The openings 39 and 40 may further be provided with arrow-like indicia, shown at 41 which, in conjunction with number indicia 42, will enable the surgeon to make a relatively accurate approximation of the number of staples remaining in the row 11 (see also FIG. 3).

The upper edges of side walls 37 and 38 are longitudinally notched as at 43 and 44, respectively. These notches are adapted to cooperate with the appropriate one of the body notches 33 and 34 (FIG. 4). Similarly, front wall 36 has an upper surface 45 adapted to abut the lowermost edge of body front wall 23 (see FIGS. 3 and 4).

Figure 21:
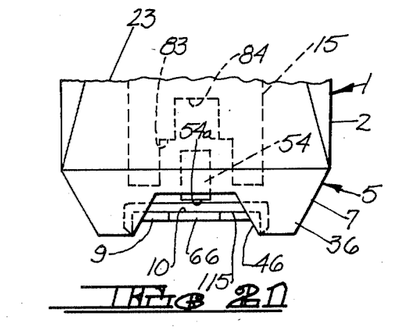
FIG. 21 is a fragmentary front elevational view of the present invention illustrating the staple driver in its retracted position.
Figure 22:
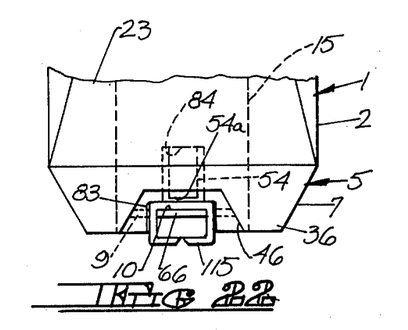
FIG. 22 is a fragmentary front elevational view, similar to FIG. 21, and illustrating the staple driver in its staple forming position.

Front wall 36 has formed therein a notch 46. This notch is shown in FIGS. 2, 21 and 22, as well as in FIGS. 5 and 6. The purpose of this notch will be apparent hereafter. The bottom 35 terminates short of front wall 36, forming the opening 47. The inside surface 48 of front wall 36 slopes upwardly and rearwardly and constitutes a part of the driver channel 14 (see FIG. 3). Finally, the upper surface of bottom 35 is provided with a plurality of substantially conical depressions, shown at 49 in FIG. 6. The purpose of these depressions will be apparent in the discussion of the upper member 8 of magazine 5, next to follow.

Figure 7:
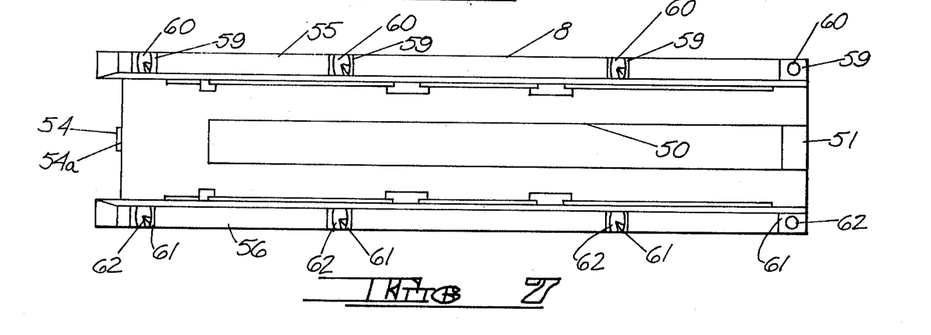
FIG. 7 is a bottom view of the upper member of the surgical staple magazine.
Figure 8:
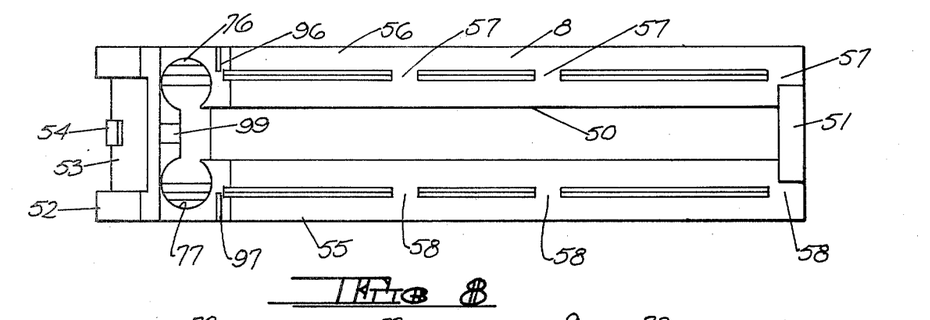
FIG. 8 is a top plan view of the upper member of the magazine.

The upper member 8 of the magazine 5 is shown from both the bottom and top in FIGS. 7 and 8, respectively. The upper member 8 constitutes an elongated structure having a longitudinal slot 50 extending from its rearward end toward its forward end. At the rearward end of upper member 8 the slot 50 is spanned by an inverted U-shaped member 51. At its forward end the upper member terminates in an upwardly and rearwardly sloping wall 52 having a notch 53 formed therein. The notch 53 is of a width to just nicely accommodate the staple driver 15. The notch 53 forms a part of the staple driver channel 14 (see FIG. 3). Centrally of notch 53 there is located a lug 54, the lowermost surface 54a of which serves as a staple retaining surface, as will be later described.

Extending rearwardly of front wall 52, the upper magazine member 8 is provided along each of its sides with a downwardly depending side wall. The side walls are shown at 55 and 56 in FIGS. 7, 8 and 13. The side walls 55 and 56 are integral with front wall 52 and are at the same time integral with the remainder of upper member 8 by virtue of webs 57 and 58. The lowermost edge of side wall 55 is provided with a plurality of lugs 59 which extend downwardly from the side wall 55 by a distance subsantially equivalent to the thickness of anvil plate 9 (FIG. 3). Each lug 59 has a substantially conical extension 60. In similar fashion, the lower edge of side wall 56 is provided with a plurality of lugs 61, equivalent to the lugs 59 and having conical extensions 62 equivalent to conical extensions 60. As is true of lower member 7, upper member 8 lends itself well to being molded of a plastic material appropriate for use in a surgical environment.

Figure 9:
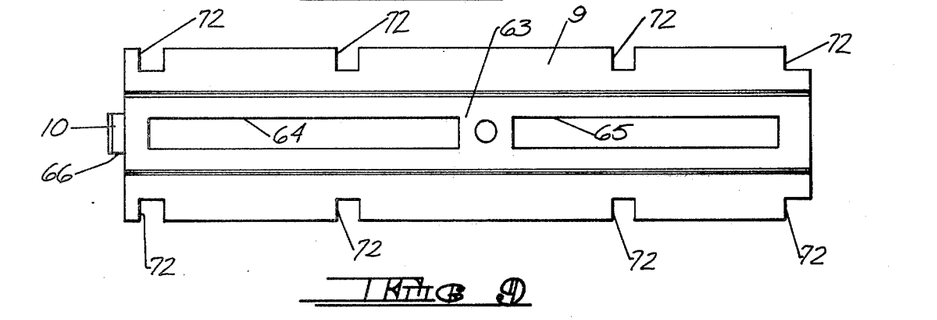
FIG. 9 is a top plan view of the anvil plate of the present invention.

The anvil plate 9 is shown in plan in FIG. 9. The anvil plate 9 is preferably formed of an appropriate metal for use in a surgical environment, such as stainless steel or the like. The anvil plate 9 has a cross section approximating that of the bottom 35 of lower magazine member 7. To this end, the anvil plate 9 has a longitudinally extending raised center portion 63. The raised central portion 63 is provided with a pair of longitudinal slots 64 and 65, corresponding to the longitudinal slots 39 and 40 in the lower magazine member 7. Slots 64 and 65 also enable the surgeon to view the row of staples 11 from the underside of magazine 5.

At its forwardmost end the anvil plate 9 is provided with an extension 66. The extension 66 is an integral, one-piece part of the raised central portion 63 and lies at a slight angle thereto. This can readily be seen in FIG. 3. The upper surface of extension 66 constitutes anvil surface 10 which is coextensive with the upper surface of the central raised portion 63 of the anvil plate and is angled slightly upwardly and outwardly therefrom, as indicated above. The central raised portion 63 of anvil plate 9 is of such width and height that it can be conveniently straddled by the staples of row 11. The central raised portion 63 is also intended to be straddled by feeder shoe 12 (see FIG. 3).

Figures 10, 11:
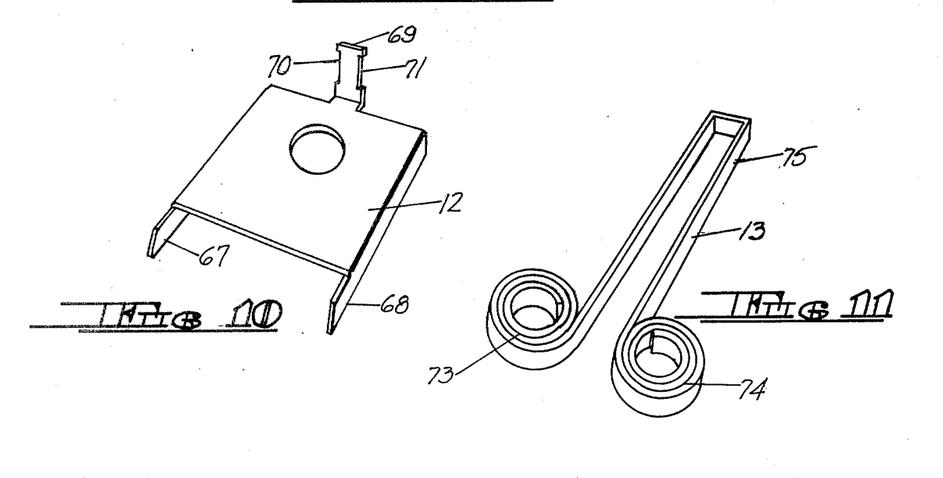
FIG. 10 is a perspective view of the magazine feeder shoe.
FIG. 11 is a perspective view of the magazine double-coil spring.

Feeder shoe 12 is most clearly shown in FIG. 10, the feeder shoe comprises a substantially planar element having downwardly depending legs 67 and 68. At its rearward edge, the feeder shoe 12 is provided with an upstanding lug 69 notched at its vertical edges, as at 70 and 71. The feeder shoe 12 is preferably made of metal such as stainless steel.

In assembling the staple magazine 5, the anvil plate 9 is first inserted in the lower magazine member 7, resting upon the bottom 35 thereof. Returning to FIG. 9, it will be noted that the longitudinal edges of anvil plate 9 are provided with a plurality of notches 72. When the anvil plate is located in the lower magazine member 7, the notches 72 will expose the depressions 49 formed in the bottom 35 of the lower magazine member 7. Also, as stated above, the longitudinal slots 64 and 65 of anvil plate 9 will overlie the longitudinal slots 39 and 40 of the lower magazine member 7.

Figure 12:
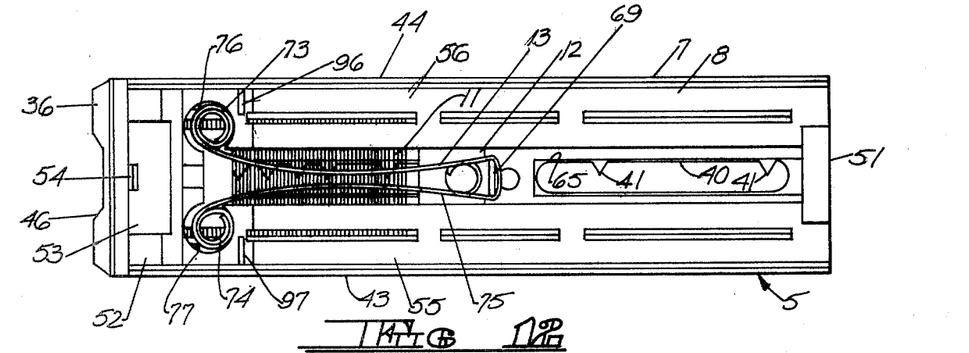
FIG. 12 is a top plan view of the assembled magazine.

Thereafter, the upper magazine member 8 is located in and fits just nicely within the lower magazine member 7, as is shown in FIG. 12. The upper magazine member 8 will overlie anvil plate 9 and will be spaced upwardly therefrom by a distance sufficient to accommodate the row of staples 11. The lower edges of side walls 55 and 56 of the upper magazine member will rest upon the longitudinal edges of anvil plate 9. The anvil plate notches 72 are sized so as to permit the passage therethrough of the lugs 59 of side walls 55 and the lugs 61 of side wall 56 of the upper magazine member 8. The conical extensions 60 and 62 are received within the depressions 49 of lower magazine member 7 and may be appropriately affixed therein by welding, adhesive means or the like. The passage of the upper magazine member lugs 59 and 61 through the notches 72 of the anvil plate 9 will lock the anvil plate in its proper position within the magazine 5.

It will be noted from the Figures, and particularly FIG. 3, that the front wall 52 of the upper magazine member 8 will abut the inside surface 48 of the lower magazine member front wall 36. As a result of this, the remainder of the inside surface 48 of the lower magazine member front wall 36 and the notch 53 in the front wall 52 of the upper magazine member 8 will form the driver channel 14 shown in FIG. 3. The anvil surface 10 of the anvil plate extension 66 will lie directly under the driver channel 14. The lug 54 in the notch 53 at the forward end of the upper magazine member 8 will also abut the inside surface 48 of the front wall 36 of the lower magazine member 7. Its staple retaining surface 54a will be oriented in parallel spaced relationship to anvil surface 10.

With the magazine elements 7, 8 and 9 thus assembled, a row of staples 11 may be introduced therein from the rearward end of the magazine. As indicated above, each staple of row 11 is adapted to straddle the raised central portion 63 of anvil plate 9. The row of staples 11 is enclosed by virtue of the fact that the upper magazine portion 8 overlies all but the longitudinal central portion of the row of staples 11.

With the row 11 of staples located within the magazine 5, the feeder shoe 12 may next be inserted into the magazine at its rearward end. As is true of the row 11 of staples, the feeder shoe 12 is intended to straddle the raised central portion 63 of anvil plate 9. In similar fashion, the upper magazine member 8 overlies the feeder shoe 12. The upstanding lug 69 of the feeder shoe will extend upwardly through the longitudinal slot 50 of the upper magazine member 8. The inverted U-shaped portion 51 of the upper magazine member 8 is of such height as to permit the feeder shoe lug 69 to pass thereunder.

The purpose of feeder shoe 12 is to constantly urge the row 11 of staples toward anvil surface 10 of anvil plate 9 to located the forwardmost staple of row 11 on anvil surface 10. When the forwardmost staple is formed about anvil surface 10 by staple driver 15, the next succeeding staple of row 11 will be shifted by feeder shoe 12 to anvil surface 10, assisting in the disengagement of the formed staple therefrom. To enable this action of feeder shoe 12, the double-coil spring 13 is provided. The spring is most clearly shown in FIG. 11. It comprises a pair of coils 73 and 74 which are formed from the same band of coil spring material and therefore are interconnected. The coils 73 and 74 are biased to their coiled condition and hence resist being uncoiled. Nevertheless, they may be uncoiled to form a loop 75 therebetween. The loop 75 is configured to extend about the upstanding lug 69 of feeder shoe 12, engaging the notches 70 and 71 therein.

Turning to FIG. 8, it will be noted that the upper surface of the upper magazine member 8, immediately behind front wall 52, has a pair of circular sockets 76 and 77 formed therein. As is most clearly shown in FIG. 12, the sockets 76 and 77 are adapted to accommodate coils 73 and 74, respectively. The tendency of coil 73 and 74 to tighten will cause the loop portion 75 of spring 13 to constantly urge feeder shoe 12 and thus the row of staples 11 toward the forward end of the cartridge 5 and toward the anvil surface 10.

Figure 14:
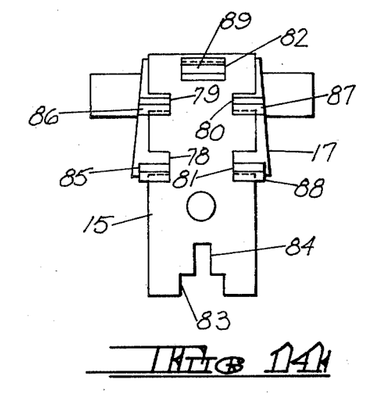
FIG. 14 is a front elevational view of the staple driver-staple driver actuator assembly.
Figure 15:
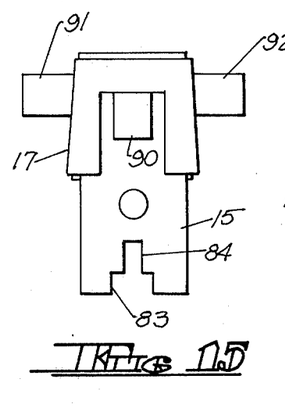
FIG. 15 is a rear elevational view of the staple driver-staple driver actuator assembly.

Reference is now made to FIGS. 14 and 15 wherein the assembly of the staple driver 15 and the staple driver actuator 17 is illustrated. Staple driver 15 comprises an elongated plate preferably made of metal suitable for a surgical environment such as stainless steel or the like. The plate is provided with a series of notches 78 through 81 extending inwardly from its longitudinal sides. It is also provided, at its upper end, with a rectangular perforation 82. At its lowermost end, the staple driver 15 has a first notch 83 formed therein. This notch is so sized as to cause the forming of a staple about anvil surface 10, as will be described hereinafter. The notch 83 leads to a second and narrower notch 84 which simply serves as a clearance notch for the lug 54 in the staple driver channel 14 of magazine 5.

The staple driver actuator 17 comprises an inverted U-shaped element which may be molded of appropriate plastic material. On its forward face, the staple driver actuator 17 is provided with a plurality of undercut forwardly extending lugs 85 through 88 adapted to be accommodated in staple driver notches 78 through 81, respectively. Near its upper end the forward face of staple driver actuator 17 is provided with yet another undercut lug 89. It will be noted that the lug 89 is undercut oppositely from the manner in which lugs 85 through 88 are undercut. The lug 89 is resilient and is adapted to extend through the rectangular perforation 82 in staple driver 14. In this way, each of lugs 85 through 89 of staple driver actuator 15 cooperates with its respective one of notches 78 through 81 and perforation 82 in staple driver 15 to provide a snap engagement of the staple driver actuator 17 on the staple driver 15.

The staple driver actuator 17 has a centrally located, downwardly depending cylindrical lug 90 which constitutes a seat for the upper end of return spring 18 (see FIG. 3). The staple driver actuator 17 also has a pair of coaxial, laterally extending, cylindrical lugs 91 and 92 which are intended to extend through the slots 28 and 29, respectively, of the forward portion 4 of the instrument body 2. The lugs 91 and 92 enable engagement of the staple driver actuator 15 by trigger 6, as will be shown.

Figure 16:
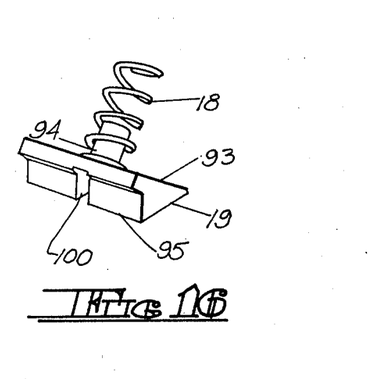
FIG. 16 is a perspective view of the return spring and its seat.
Figure 17:
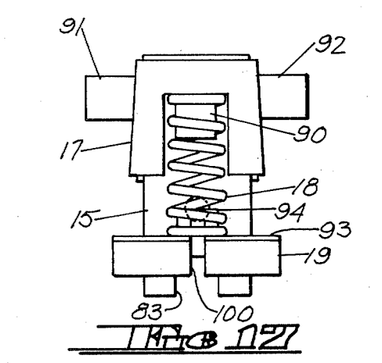
FIG. 17 is an elevational view illustrating the assembly of the staple driver, staple driver actuator, return spring and return spring seat.

In FIG. 16, return spring 18 is illustrated together with the seat 19 therefor. The return spring 18 is a metallic coil compression spring. The spring seat 19 has an upper surface 93 from which extends a cylindrical lug 94 adapted to be inserted in the lower end of return spring 18 to maintain that end of the return spring in place. FIG. 17 illustrates the assembly of the staple driver 15, staple driver actuator 17, return spring 18 and spring seat 19. It will be noted that the upper end of return spring 18 receives the cylindrical lug 90 of the staple driver actuator 17. Thus, return spring 18 is maintained in place by lugs 90 and 94 and will tend to urge the staple driver actuator 17 away from spring seat 19, thus urging the staple driver 15 to its retracted position shown in FIG. 3.

The spring seat 19 has a flat bottom surface 95 and is adapted to be supported on that area of the upper magazine member 8 surrounding sockets 76 and 77 (see FIGS. 8 and 12). When so located, the spring seat lies between the rear surface of the forward wall 52 of the upper magazine member 8 and a pair of lugs 96 and 97 formed on the upper surface of the upper magazine member 8 just behind sockets 76 and 77. To assure that the spring seat is properly centered on the upper magazine member 8, the upper magazine member 8 has a lug 99 extending rearwardly of the rear surface of its forward wall 52. This lug 99 is adapted to be received in a slot 100 in the spring seat 19 (see FIGS. 16 and 17). It will be noted by one skilled in the art that once the spring seat 19 is properly located on the upper magazine member 8, as shown in FIG. 3, it will overlie sockets 76 and 77 thus serving to maintain the coils 73 and 74 of spring 13 in the sockets.

Figure 18:
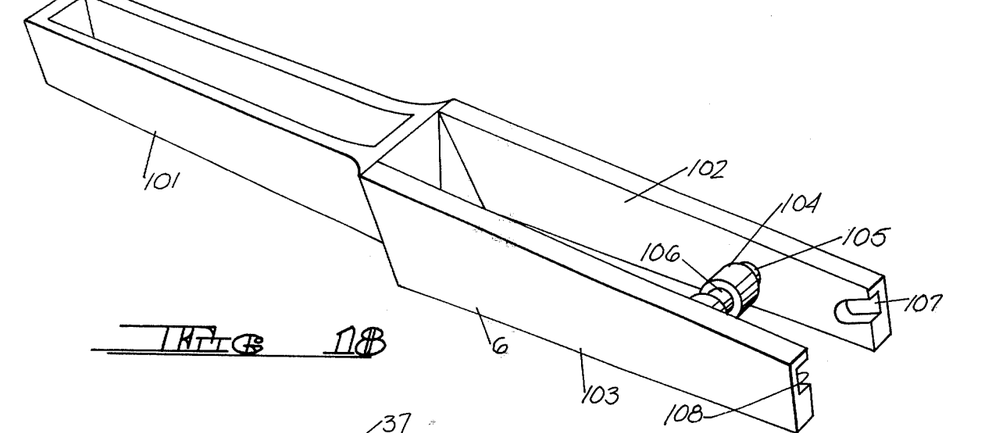
FIG. 18 is a perspective view of the trigger of the present invention.

Reference is now made to FIG. 18 wherein trigger 6 is most clearly shown. The trigger 6 has a rearward portion 101 constituting a handle portion. The forward portion of trigger 6 is bifurcated, bifurcations 102 and 103 lying in parallel spaced relationship. As in the case of body 2, the trigger 6 may be molded of an appropriate plastic material. The trigger 6 is provided with a pivot pin 104 which joins and is an integral part of bifurcations 102 and 103. The pin 104 is of reduced diameter immediately adjacent bifurcation 102, as at 105. It is similarly of reduced diameter immediately adjacent bifurcation 103 (not shown). The portion 105 of reduced diameter is adapted to be received in notch 27 in side wall 22 of the instrument body 2 (see FIG. 4). The portion of reduced diameter (not shown) adjacent bifuraction 103 is similarly intended to be received within the notch 26 in side wall 21 of instrument body 2. When the magazine 5 is mounted on the forward portion 4 of instrument body 2 the enlarged portions of pivot pin 104 will rest upon the upper surface of the magazine. In this way, the trigger 6 is pivotally affixed to the instrument body 2 and is held in place by the magazine 5. The central portion of pivot pin 104 may also be of reduced diameter, as at 106. This will provide clearance for the upstanding lug 69 of feeder shoe 12.

The forwardmost ends of bifurcations 102 and 103 are provided with slots which do not pass completely through the bifurcations. These slots are shown in FIG. 18 at 107 and 108. The slots 107 and 108 are intended to just nicely receive the ends of cylindrical lugs 91 and 92 of the staple driver actuator 17, the ends of lugs 91 and 92 extending beyond the instrument body side walls 21 and 22 through slots 28 and 29 therein, respectively. As a consequence, the trigger 6 is pivotally affixed to the instrument body 2 and is operatively connected to the staple driver actuator 17 and thus staple driver 15.

Turning to FIGS. 1 and 3, the surgical stapling instrument is therein shown in its normal, un-actuated condition. The staple driver 15 and staple driver actuator 17 are in their retracted positions and trigger 6 is in its normal position. These elements are maintain in these positions by return spring 18. It will be evident from FIGS. 1 and 2, however, that if trigger 6 is shifted to its actuated position in abutment with lug 25 at the rearward end of instrument body 2, it will pivot in a counter-clockwise direction about pivot pin 104 (as viewed in FIGS. 1 and 3). The forward ends of bifurcations 102 and 103, by virtue of their engagement with lugs 91 and 92 of staple driver actuator 17 will cause the staple driver actuator 17 and thus staple driver 15 to shift downwardly within the forward portion 4 of the instrument body 2, the lower end of staple driver 15 shifting downwardly in staple driver channel 14 toward anvil surface 10 and to its staple forming position.

During shifting of the staple driver 15 (and hence staple driver actutor 17) between its retracted and its staple forming positions, the trigger bifurcation slots 107 and 108 are so sized as to cause staple driver actuator lugs 91 and 92 to ride along those portions 28a of slot 28 and 29a of slot 29. This will assure that that portion of staple driver 15 between staple driver actuator lugs 78 through 81 will ride against the integral guide rails 30 and 31 of the instrument body forward wall 23. Guide rails 30 and 31 are spaced so as to be just nicely received between the staple driver actuator lugs 78 and 79 and the staple driver actuator lugs 80 and 81 with staple driver actuator lug 82 located between rails 30 and 31. All of this assures that the staple driver shifts between its retracted and its staple forming positions in proper alignment with the staple driver channel 14.

Figure 19:
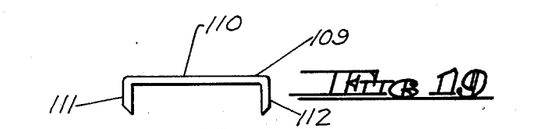
FIG. 19 is an elevational view of a surgical staple for use with the surgical stapling instrument of the present invention.
Figure 20:
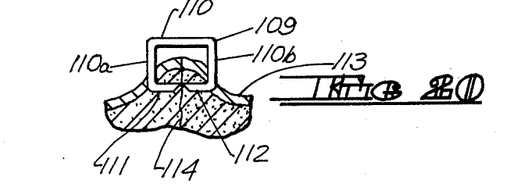
FIG. 20 is an elevational view, partly in cross section, illustrating the staple of FIG. 19 in its fully formed condition implanted in the skin of a patient.

In FIG. 19 there is shown a typical surgical staple for use with the instrument of the present invention. The staple is shown in its unformed condition and is generally indicated at 109. Initially, the staple comprises an elongated crown 110 and a pair of downwardly depending legs 111 and 112 which, at their forwardmost ends are diagonally cut so as to be pointed. In FIG. 20, the staple of FIG. 19 is shown in its fully formed condition and implanted in the skin 113 of a patient to suture the wound 114. In its fully formed condition, the legs 111 and 112 of the staple are inturned and opposed, portions 110a and 110b of the original crown 110 having been bent downwardly. It is this downward bending of the staple portions 110a and 110b that is accomplished by staple driver 15, the staple driver 15 bending the portions 110a and 110b of staple 109 about anvil surface 10.

The surgical stapling instrument of the present invention comes to the surgeon with its magazine containing a predetermined number of staples and the entire assembly having been appropriately sterilized.

FIG. 21 is a fragmentary front elevational view of the surgical stapling instrument of the present invention illustrating the instrument body, 2 the surgical staple driver 15 and the magazine 5. In FIG. 21, a forwardmost staple 115 of the row 11 thereof is shown mounted on the anvil surface 10 of the extension 66 of anvil plate 9. As indicated above, since the anvil surface 10 is an integral, one-piece part of anvil plate 9 and by virtue of feeder shoe 12 and doublecoil spring 13, the forwardmost staple of the row 11 thereof will always be properly located on anvil surface 10. It will be evident from FIG. 21 that the unformed forwardmost staple 115 is wider than the notch 46 in the forwardmost wall 36 of the magazine lower member 7 and therefor is maintained on anvil surface 10 by virtue of its abutment against the inside surface 48 of the forwardmost wall 36 of the lower magazine member 7 and by abutment with the row of staples behind it.

The surgeon need only properly locate the surgical stapling instrument over the wound, utilizing the indicia arrow 32 (FIG. 2) as a guide. Once the instrument 1 is properly located, the surgeon shifts trigger 6 from its normal position to its actuated position. As explained above, this will cause a downward shifting of staple driver actuator 17 which, in turn, will cause shifting of staple driver 15 from its normal position to its staple forming position.

FIG. 22 differs from FIG. 21 only in that the staple driver 15 is illustrated in its staple forming position. By virtue of the engagement of the crown of staple 115 by the staple driver notch 83, the staple will be formed about anvil surface 10 in the manner described with respect to FIG. 20. During the initial bending of the crown of staple 115, its tendency to arch or bow upwardly and away from anvil surface 10 will be precluded by staple retaining surface 54a of the lug 54 of upper magazine member 8.

When the staple 115 is fully formed as shown in FIG. 22 it will be firmly implanted in the skin or fascia of the patient. The surgeon thereafter releases his grip on trigger 6, permitting it to be returned to its normal position by return spring 18. At the same time, the staple driver actuator 17 will return to its retracted position and staple driver 15 will shift from its staple forming position to its retracted position in staple driver channel 14. It will be evident from FIG. 22 that staple 115 in its fully formed condition can now readily pass through the notch 46 in the front wall 36 of the lower magazine member 7. The forward urging of the next succeeding staple in the row 11 thereof by feeder shoe 12 and its spring 13 will cause the next succeeding staple to assist the fully formed staple to become disengaged from anvil surface 10. The surgical stapling instrument is then in condition to form and implant the next staple.

From the above description it will be evident that the force required to shift trigger 6 from its normal to its actuated position is only that much as is required to shift the driver from its retracted to its staple forming position, resulting in the forming of the forwardmost staple about anvil surface 10. No part of the force applied to the trigger is required to shift a staple to the anvil surface 10 since this is accomplished solely and automatically by the feeder shoe 12 and its spring 13.

The surgical stapling instrument of the present invention has been described in its disposable form, all parts of the surgical stapling instrument (with the exception of the anvil plate 9, feeder shoe 12, spring 13, return spring 18 and staple driver 15) being readily formable of an appropriate plastic material. It, of course, would be within the skill of the worker in the art to make the surgical stapling instrument of the present invention in a reusable form. This would require that means be provided to detachably mount the magazine 5 on the instrument body 2 so that it could be replaced. Similarly, the upper and lower members 7 and 8 of the magazine 5 could be detachably affixed together so that the magazine could be disassembled for reloading.

Modifications may be made in the invention without departing from the spirit of it.

The embodiments of the invention in which an exclusive property or privilege is claimed are defined as follows:

1. A surgical stapling instrument for implanting and forming surgical staples in the skin or fascia of a patient, said instrument comprising an elongated body having a rearward portion constituting a handle portion and a forward portion, a staple driver and a staple driver actuator attached to said staple driver being housed within said body forward portion, a surgical staple magazine affixed to said body forward portion, an anvil plate mounted within said magazine, said anvil plate terminating at its forward end in a coextensive anvil surface, a row of staples slidably mounted on said anvil plate, a feeder assembly mounted in said magazine to constantly urge and advance said row of staples along said anvil plate toward said anvil surface to locate the forwardmost staple of said row thereon to be implanted and formed thereabout by said driver and to disengage said forwardmost staple therefrom when formed, said staple driver being shiftable between a retracted position above said anvil surface and a staple forming position wherein it forms said forwardmost staple about said anvil surface, trigger means to shift said staple driver between said retracted and said staple forming positions, said trigger means being pivotally affixed to said body and operatively connected to said staple driver by way of said staple driver actuator, and means to bias said staple driver to said retracted position.

2. The structure claimed in claim 1 wherein said feeder assembly mounted in said magazine to constantly urge and advance said row of staples along said anvil plate toward said anvil surface is independent of said trigger means.

3. The structure claimed in claim 1 wherein each staple of said row thereof comprises an elongated horizontal crown portion terminating at each of its ends in a downwardly depending leg portion, and including staple retaining means overlying said anvil surface to control the amount of bending of said crown portion of a staple being formed by said staple driver.

4. A surgical stapling instrument for implanting and forming surgical staples in the skin or fascia of a patient, said instrument comprising an elongated body having a top, sides and forward and rearward ends, said body having a rearward portion constituting a handle portion and a forward portion, a staple driver and a staple driver actuator attached to said staple driver being housed within said body forward portion, a surgical staple magazine affixed to said body forward portion at the lower edges of said body forward end and sides, an anvil plate mounted within said magazine and extending substantially the length thereof, said anvil plate terminating at its forward end in a coextensive anvil surface, a row of staples slidably mounted on said anvil plate, a feeder assembly mounted in said magazine to constantly urge and advance said row of staples along said anvil plate toward said anvil surface to locate the forwardmost staple of said row thereon to be implanted and formed thereabout by said driver and to disengage said forwardmost staple therefrom when formed, said magazine forming a channel for the lower end of said staple driver, said anvil surface being located beneath said channel, said staple driver being shiftable between a retracted position above said anvil surface and a staple forming position wherein it forms said forwardmost staple about said anvil surface, trigger means to shift said staple driver between said retracted and said staple forming positions, said trigger means being pivotally affixed to said body forward portion and operatively connected to said staple driver actuator, said trigger means being pivotable between a normal position wherein said staple driver is in its retracted position and an actuated position wherein said staple driver is in said staple forming position, and means to bias said staple driver to said retracted position and said trigger means to said normal position.

5. The structure claimed in claim 4 wherein said feeder assembly mounted in said magazine to constantly urge and advance said row of staples along said anvil plate toward said anvil surface is independent of said trigger means.

6. The structure claimed in claim 4 including a pair of lugs on said staple driver actuator extending laterally to either side thereof, each of said staple driver actuator lugs extending through a slot in the adjacent one of said body sides, said trigger means having a rearward handle portion and a bifurcated forward portion, the bifurcations being located to either side of said body forward portion and being pivoted thereto, each of said bifurcations having a free end provided with a slot so sized as to receive the end of one of said staple driver actuator lugs.

7. The structure claimed in claim 4 wherein said means to bias said staple driver to its retracted position and said trigger means to its normal position comprises a compression spring, a seat for one end of said compression spring, said seat being mounted on said surgical staple magazine, the other end of said compression spring engaging said staple driver actuator.

8. The structure claimed in claim 4 wherein said surgical staple magazine comprises upper and lower elongated members, said lower member having a bottom, side walls and a front wall spaced from said bottom, said anvil plate being mounted within said lower member on said bottom thereof and extending longitudinally thereof, said upper member having a top, downwardly depending side walls and a front wall having a forward face with a notch formed therein and extending from top to bottom thereof, said notch being of a width to accommodate said lower end of said staple driver, said upper member being mounted within said lower member above said anvil plate and with said forward face of its front wall abutting said front wall of said lower member, said notch in said forward face of said upper member front wall and said front wall of said lower member defining said channel for said lower end of said staple driver, a row of surgical staples slidably mounted on said anvil plate and beneath said upper member, said front wall of said lower member having a notch formed therein of such width as to permit the passage therethrough of a staple from said anvil surface only after said staple has been formed about said anvil surface.

9. The structure claimed in claim 8 wherein said feeder assembly comprises a feeder shoe and spring therefor, said feeder shoe being slidably mounted on said anvil plate behind said row of staples and beneath said upper member, said top of said upper member having a longitudinal slot therein, a lug on said feeder shoe extending upwardly through said slot in said top of said magazine upper member, said spring being mounted at the forward end of said top of said upper member, said spring engaging said lug of said feeder shoe to constantly urge said feeder shoe forwardly along said anvil plate.

10. The structure claimed in claim 8 wherein each staple of said row thereof comprises an elongated horizontal crown portion terminating at its ends in downwardly depending leg portions, and including a lug located in and centrally of said notch formed in said forward face of said upper member, said lug overlying said anvil surface and comprising a staple retaining means to control the amount of bending of said crown portion of a staple being formed by said staple driver.

11. The structure claimed in claim 9 wherein said spring comprises a ribbon of spring metal spirally coiled at both ends, said forward end of said top of said magazine upper member having a pair of sockets formed therein, each of the coils being located in one of said sockets, an intermediate portion of said spring passing about and engaging said feeder shoe lug.

12. The structure claimed in claim 9 wherein said staple driver, said anvil plate, said feeder shoe, said feeder shoe spring and said means to bias said staple driver and said trigger means are metallic, the remainder of said surgical stapling instrument being molded of plastic material.

13. The structure claimed in claim 9 including a pair of lugs on said staple driver actuator extending laterally to either side thereof, each of said staple driver actuator lugs extending through a slot in the adjacent one of said body sides, said trigger means having a rearward handle portion and a bifurcated forward portion, the bifurcations being located to either side of said body forward portion and being pivoted thereto, each of said bifurcations having a free end provided with a slot so sized as to receive the end of one of said staple driver actuator lugs.

14. The structure claimed in claim 9 wherein said means to bias said staple driver to its retracted position and said trigger means to its normal position comprises a compression spring, a seat for one end of said compression spring, said seat being mounted on said surgical staple magazine, the other end of said compression spring engaging said staple driver actuator.

15. The structure claimed in claim 9 wherein said lower member of said magazine has at least one central longitudinal slot in said bottom thereof, said anvil plate having at least one central longitudinally extending slot therein overlying said at least one slot in said lower member, whereby said row of staples can be viewed from the underside of said magazine.

16. The structure claimed in claim 11 wherein said means to bias said staple driver to its retracted position and said trigger to its normal position comprises a compression spring, a seat for one end of said compression spring, said seat being mounted on said top of said upper magazine member overlying said sockets and said feeder shoe spring coils therein, the other end of said compression spring engaging said staple driver actuator.

* * * * *